US012773484B2

(12) United States Patent
Hansen et al.

(10) Patent No.: US 12,773,484 B2
(45) Date of Patent: Oct. 27, 2026

(54) EXTRACORPOREAL MEMBRANE OXYGENATOR WITH PARTITIONED SIDES

(71) Applicant: TC1 LLC, St. Paul, MN (US)

(72) Inventors: J. Freddy Hansen, Alameda, CA (US); Daniel I. Harjes, Carlisle, MA (US)

(73) Assignee: TC1 LLC, St. Paul, MN (US)

( * ) Notice: Subject to any disclaimer, the term of this patent is extended or adjusted under 35 U.S.C. 154(b) by 331 days.

(21) Appl. No.: 18/489,158

(22) Filed: Oct. 18, 2023

(65) Prior Publication Data

US 2024/0123131 A1 Apr. 18, 2024

Related U.S. Application Data

(60) Provisional application No. 63/417,211, filed on Oct. 18, 2022.

(51) Int. Cl.

| | |
|---|---|
| ***A61M 1/16*** | (2006.01) |
| ***B01D 63/04*** | (2006.01) |
| ***B01D 69/08*** | (2006.01) |

(52) U.S. Cl.
CPC ........ *A61M 1/1698* (2013.01); *A61M 1/1625* (2014.02); *A61M 1/1629* (2014.02);
(Continued)

(58) Field of Classification Search
CPC .............. A61M 1/3667; A61M 1/1625; A61M 1/1698; A61M 1/3666; A61M 60/113; A61M 60/232; A61M 60/38; A61M 60/419; A61M 60/422; A61M 60/82; A61M 60/824; A61M 60/825; A61M 2205/7536; A61M 1/267; A61M 1/1629; A61M 2202/0007; A61M 2202/0014; A61M 2202/0028; A61M 2202/0208; A61M 2202/0225; A61M 2206/12; A61M 2205/3368; A61M 2205/366; B01D 63/04; B01D 69/08; B01D 2313/08; B01D 2313/221; B01D 2315/24; Y10S 261/28
See application file for complete search history.

(56) References Cited

U.S. PATENT DOCUMENTS 2,972,349 A 2/1961 De
3,794,468 A 2/1974 Leonard
(Continued)

*Primary Examiner* — Guy K Townsend
*Assistant Examiner* — Alessandro R Del Priore
(74) *Attorney, Agent, or Firm* — Kilpatrick Townsend & Stockton LLP

(57) ABSTRACT

An oxygenator and method for oxygenating blood. The oxygenator includes a housing, an oxygenation chamber, and elongated gas permeable conduits that extend across the oxygenation chamber. The blood flow enters and contacts with exterior surfaces of the conduits and exits the oxygenator to transfer of oxygen from within the conduits to the blood flow and transfer carbon dioxide from the blood flow into the elongated gas permeable conduits. The housing includes a gas inlet and is configured to distribute a gas flow received through the gas inlet to the elongated gas permeable conduits so as to a first portion of the gas flow flows through a first set of the elongated gas permeable conduits in a first direction and a second portion of the gas flow flows through a second set of the elongated gas permeable conduits in a second direction that is opposite to the first direction.

12 Claims, 12 Drawing Sheets

(52) U.S. Cl.
CPC ............. *B01D 63/04* (2013.01); *B01D 69/08* (2013.01); *A61M 2202/0007* (2013.01); *A61M 2202/0014* (2013.01); *A61M 2202/0028* (2013.01); *A61M 2202/0208* (2013.01); *A61M 2202/0225* (2013.01); *A61M 2206/12* (2013.01); *Y10S 261/28* (2013.01)

(56) References Cited

U.S. PATENT DOCUMENTS

| | | | | |
|---|---|---|---|---|
| 4,239,729 | A | 12/1980 | Hasegawa et al. | |
| 4,374,802 | A | 2/1983 | Fukasawa | |
| 4,975,247 | A | 12/1990 | Badolato et al. | |
| 5,217,689 | A | 6/1993 | Raible | |
| 5,266,265 | A | 11/1993 | Raible | |
| 5,270,005 | A | 12/1993 | Raible | |
| 5,429,486 | A | 7/1995 | Schock et al. | |
| 5,770,149 | A | 6/1998 | Raible et al. | |
| 6,454,999 | B1 * | 9/2002 | Farhangnia | F28F 21/062 604/6.14 |
| 6,730,267 | B2 | 5/2004 | Stringer et al. | |
| 6,936,222 | B2 | 8/2005 | Mortensen et al. | |
| 10,258,729 | B2 | 4/2019 | Gellman et al. | |
| 2004/0223872 | A1 * | 11/2004 | Brian | A61M 1/1698 604/6.14 |
| 2019/0134294 | A1 * | 5/2019 | Reichl | A61M 1/169 |
| 2021/0393941 | A1 | 12/2021 | Hansen | |

* cited by examiner

EXTRACORPOREAL MEMBRANE OXYGENATOR WITH PARTITIONED SIDES

CROSS REFERENCE TO RELATED APPLICATION DATA

The present application claims the benefit of U.S. Provisional Appln No. 63/417,211 filed Oct. 18, 2022; the full disclosure which is incorporated herein by reference in its entirety for all purposes.

FIELD OF DISCLOSURE

This disclosure relates to extracorporeal oxygenators and extracorporeal life support systems. In particular, the disclosure relates to the oxygenator including gas permeable conduits configured to improve gas transfer to/from the blood.

BACKGROUND

A blood oxygenator can be used to oxygenate a flow of oxygen-depleted blood from a patient (e.g., a patient with chronic respiratory failure, a patient undergoing heart surgery) and the resulting oxygenated flow of blood can be returned to the patient. Many blood oxygenators, such as an extracorporeal membrane oxygenator (ECMO), pass a flow of oxygen-depleted blood over hollow gas permeable fibers through which an oxygen containing gas is routed. The hollow gas permeable fibers have a gas permeable outer wall through which oxygen from the oxygen containing gas is transferred to the flow of blood and carbon dioxide from the flow of blood is transferred to the gas within the hollow gas permeable fibers.

Existing blood oxygenators cover a range of configurational differences. Examples of blood oxygenators that employ hollow gas permeable fibers are described in U.S. Pat. Nos. 2,972,349, 3,794,468, 4,239,729 and 4,374,802. Some blood oxygenators employ hollow gas permeable fibers made of a homogeneous membrane of gas-permeable material such as silicone. Some blood oxygenators employ hollow gas permeable fibers made of a microporous membrane of hydrophobic polymeric material such as polyolefins. Blood oxygenators that employ hollow gas permeable fibers include inside perfusion type blood oxygenators and outside perfusion type blood oxygenators. In inside perfusion type blood oxygenators, the blood flow is passed through the bores of the hollow gas permeable fibers and the oxygen-containing gas is passed on the outside of the hollow gas permeable fibers. In outside perfusion type blood oxygenators, gas is passed through the bores of the hollow gas permeable fibers while blood is passed on the outside of the hollow gas permeable fibers. Examples of blood oxygenators that employ an integrated blood pump are described in U.S. Pat. Nos. 5,217,689; 5,266,265; 5,270,005; 5,770,149; 4,975,247; 5,429,486; 6,936,222; and 6,730,267.

The volume of blood required to prime a blood oxygenator is a significant consideration. Preferably, the volume of blood required is a small as possible. Accordingly, improved blood oxygenators having reduced blood priming volume remain of interest.

BRIEF SUMMARY

The present disclosure relates to extracorporeal oxygenators. In particular, the disclosure relates to the oxygenator including gas permeable conduits configured to improve gas transfer to/from the blood so that the blood is uniformly oxygenated as it passes externally over the gas permeable conduits. For example, sets of gas conduits are configured to allow gas flow in a first direction and a second direction opposite to the first direction while the blood flows in a third direction. Such bidirectional flow of gas ensures more uniform transfer of oxygen at sides as well as at a center of a blood flow. A more uniform oxygen distribution to the blood advantageously requires small priming volume and the blood experiences low shear. On the contrary, oxygenators that include other gas permeable conduits arrangements (e.g., parallel to blood flow or perpendicular to the blood flow) expose different portions of the blood flow to a different amount of available oxygen. For example, the conduits contain the most oxygen near a gas inlet, but are then depleted as the gas flows down the length of the conduits resulting in relatively low oxygenated blood near the gas outlet. Thus, existing oxygenator length needs to be longer than it would have to be if the oxygen distribution was more uniform across the blood flow cross-section. This leads to a larger priming volume, more shear on the blood, and a larger pressure drop, all of which are undesired.

Thus, in one aspect, an oxygenator for oxygenating blood is described. The oxygenator includes an oxygenator assembly and a housing. The oxygenator assembly includes a blood inlet, a blood outlet, an oxygenation chamber, and elongated gas permeable conduits that extend across the oxygenation chamber. The oxygenator assembly is configured so that a blood flow received via the blood inlet is contacted with exterior surfaces of the elongated gas permeable conduits and exits the oxygenator assembly through the blood outlet. Each of the elongated gas permeable conduits include a gas permeable outer wall configured to accommodate transfer of oxygen from within the elongated gas permeable conduit to the blood flow and transfer carbon dioxide from the blood flow into the elongated gas permeable conduits. In the oxygenator assembly, a first set of the elongated gas permeable conduits is oriented parallel to a first direction and a second set of the elongated gas permeable conduits is oriented parallel to a second direction that is transverse or opposite to the first direction. The housing includes a gas inlet and is configured to distribute a gas flow received through the gas inlet to the elongated gas permeable conduits so as to flow a first portion of the gas flow through the first set of the elongated gas permeable conduits in the first direction and flow a second portion of the gas flow through the second set of the elongated gas permeable conduits in the second direction. In many embodiments, the blood flow is perpendicular to the first direction and the second direction.

In many embodiments, the housing further includes a first inlet chamber configured to deliver the first portion of the gas flow to the first set of the elongated gas permeable conduits, and a second inlet chamber configured to deliver the second portion of the gas flow to the second set of the elongated gas permeable conduits. In many embodiments, the housing further includes a first outlet chamber configured to receive a first outlet gas flow exiting from the first set of the elongated gas permeable conduits, and a second outlet chamber configured to receive a second outlet gas flow exiting from the second set of the elongated gas permeable conduits.

In many embodiments, the housing further includes an inlet plenum, a gas outlet, and an outlet plenum. The inlet plenum is configured to receive the gas flow from the gas inlet, distribute the first portion of the gas flow to the first inlet chamber, and distribute the second portion of the gas flow to the second inlet chamber. The outlet plenum is configured to collect the first outlet gas flow from the first outlet chamber, collect the second outlet gas flow from the second outlet chamber, and deliver the first outlet gas flow and the second outlet gas flow to the gas outlet.

In many embodiments, a third set of the elongated gas permeable conduits is oriented parallel to a third direction. The housing is configured to distribute a third portion of the gas flow so as to flow through the third set of the elongated gas permeable conduits in the third direction. A fourth set of the elongated gas permeable conduits is oriented parallel to a fourth direction that is transverse to the first direction and transverse or opposite to the third direction. The housing is configured to distribute a fourth portion of the gas flow so as to flow through the fourth set of the elongated gas permeable conduits in the fourth direction. The blood flow flows through the oxygenation chamber in a blood flow direction. The third set and the fourth set of the elongated gas permeable conduits are offset from the first set and the second set of the elongated gas permeable conduits along the blood flow direction or perpendicular to the blood flow direction. The third direction is transverse to the first direction. The third direction is perpendicular to the first direction. For example, in a cuboid oxygen assembly, the first and the second direction may be between left and right sides of the cuboid, and the third and fourth directions may be between top and bottom sides of the cuboid.

In many embodiments, a fifth set of the elongated gas permeable conduits is oriented parallel to a fifth direction. The housing is configured to distribute a fifth portion of the gas flow so as to flow through the fifth set of the elongated gas permeable conduits in the fifth direction. A sixth set of the elongated gas permeable conduits is oriented parallel to a sixth direction that is transverse to each of the first direction and the third direction and transverse or opposite to the fifth direction. The housing is configured to distribute a sixth portion of the gas flow so as to flow through the sixth set of the elongated gas permeable conduits in the sixth direction. The fifth set and the sixth set of the elongated gas permeable conduits are offset from the first set, the second set, the third set, and the fourth set of the elongated gas permeable conduits along the blood flow direction. The third direction is transverse to the first direction; and the fifth direction is transverse to each of the first direction and the third direction. The third set of the elongated gas permeable conduits is angled 60 degrees relative to the first set of the elongated gas permeable conduits. The fifth set of the elongated gas permeable conduits is angled 60 degrees relative to each of the first set and the third set of the elongated gas permeable conduits. As an example, the fifth set and the sixth set of the elongated gas permeable conduits may be part of an hexagonal shaped oxygenator assembly.

In many embodiments, the oxygenation chamber has a circular, a square, a rectangular, a hexagonal, or an octagonal cross-sectional shape. The elongated gas permeable conduits comprise hollow fibers.

In many embodiments, the oxygenator further includes a heat exchanger disposed within the housing and configured to regulate a temperature of the blood flow. The housing further includes a temperature regulation fluid inlet, a temperature regulation fluid outlet, and heat exchanger conduits, a first set of the heat exchanger conduits is oriented parallel to a heat exchanger conduit first direction, a second set of heat exchanger conduits is oriented parallel to a heat exchanger conduit second direction that is transverse or opposite to the heat exchanger conduit first direction. The heat exchanger is configured so that the blood flow received via the blood inlet is contacted with exterior surfaces of the heat exchanger conduits, a first portion of a flow of temperature regulation fluid received through the temperature regulation fluid inlet flows through the first set of the heat exchanger conduits in the first direction, and a second portion of the flow of temperature regulation fluid flows through the second set of the heat exchanger conduits in the second direction.

In another aspect, a method for oxygenating blood is described. The method includes passing a blood flow received through a blood inlet of an oxygenator assembly over exterior surfaces of elongated gas permeable conduits that extend across an oxygenation chamber of the oxygenator assembly, and distributing a gas flow including oxygen received through a gas inlet of a housing to the elongated gas permeable conduits such that a first portion of the gas flow flows through a first set of the elongated gas permeable conduits in a first direction and a second portion of the gas flow flows through a second set of the elongated gas permeable conduits in a second direction that is transverse to or opposite to the first direction to transfer oxygen from the gas flow to the blood flow and to transfer carbon dioxide from the blood flow to the gas flow. In many embodiments, the blood flow flows through the oxygenator perpendicular to each of the first direction and the second direction.

In many embodiments, the housing further includes a first inlet chamber configured to deliver the first portion of the gas flow to the first set of the elongated gas permeable conduits; and a second inlet chamber configured to deliver the second portion of the gas flow to the second set of the elongated gas permeable conduits. The method further includes distributing the gas flow such that a third portion of the gas flow flows through a third set of the elongated gas permeable conduits oriented parallel to a third direction, and a fourth portion of the gas flow flows through a fourth set of the elongated gas permeable conduits oriented parallel to a fourth direction that is transverse to the first direction and transverse or opposite to the third direction. The third set and the fourth set of the elongated gas permeable conduits are offset from the first set and the second set of the elongated gas permeable conduits along the blood flow direction or perpendicular to the blood flow direction. The third direction is transverse to or perpendicular to the first direction.

In many embodiments, the method further includes distributing the gas flow such that a fifth portion of the gas flow flows through a fifth set of the elongated gas permeable conduits oriented parallel to a fifth direction, and a sixth portion of the gas flow flows through a sixth set of the elongated gas permeable conduits oriented parallel to a sixth direction that is transverse to the first direction and transverse or opposite to the fifth direction.

In many embodiments, the method further includes regulating a temperature of the blood flow by: passing a first portion of temperature regulation fluid received through a temperature regulation fluid inlet to a first set of the heat exchanger conduits oriented parallel to a heat exchanger conduit first direction, and passing a second portion of the temperature regulation fluid received through a second set of heat exchanger conduits oriented parallel to a heat exchanger conduit second direction that is transverse or opposite to the heat exchanger conduit first direction. The blood flow received via the blood inlet is contacted with exterior surfaces of the heat exchanger conduits.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and can or cannot represent actual or preferred values or dimensions.

DETAILED DESCRIPTION OF THE DISCLOSURE

Figure 1:
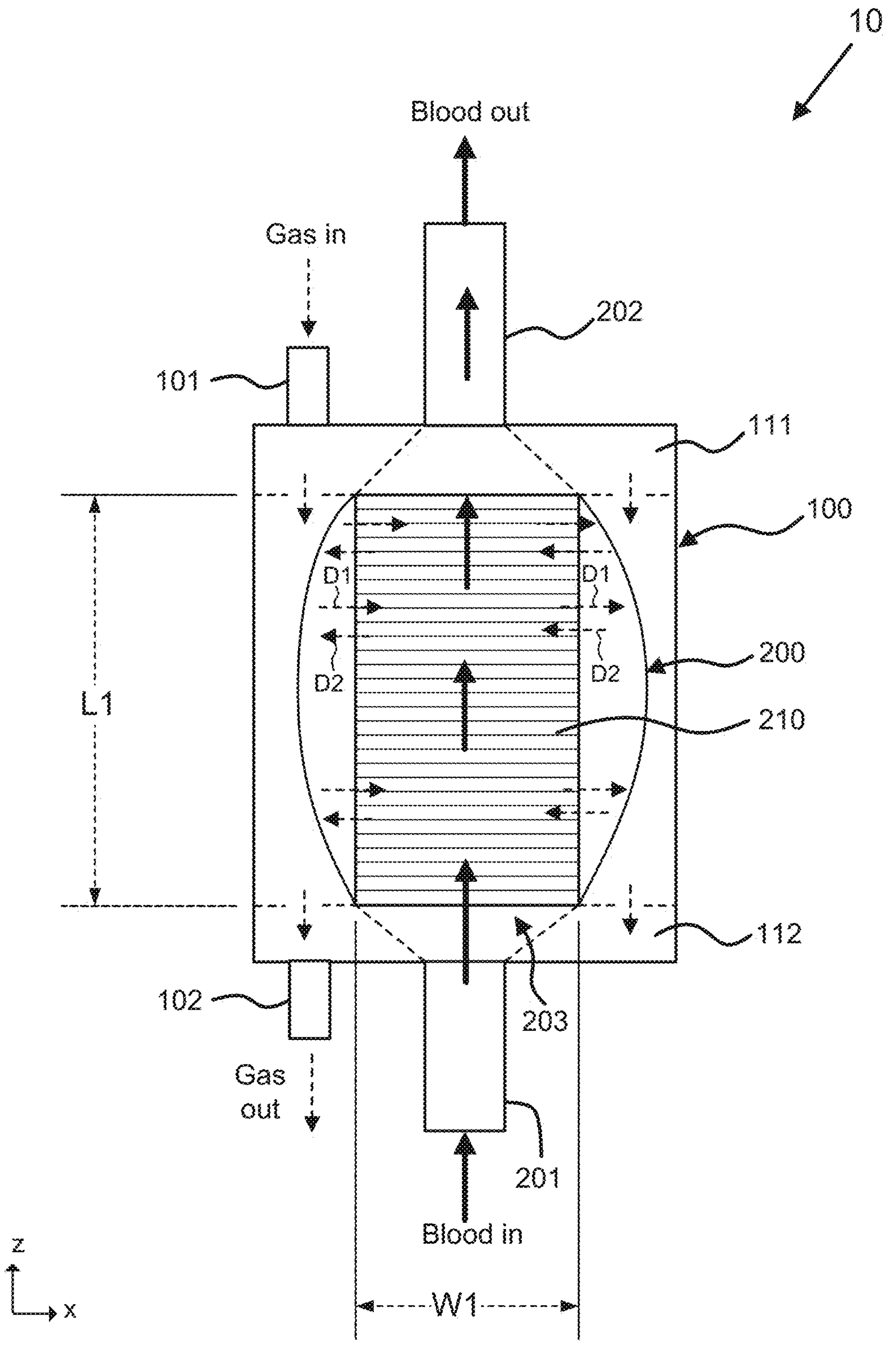
FIG. 1 illustrates an oxygenator, in accordance with many embodiments.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed embodiment(s). However, it will be apparent to those skilled in the art that the disclosed embodiment(s) can be practiced without those specific details. In some instances, well-known structures and components can be shown in block diagram form in order to avoid obscuring the concepts of the disclosed subject matter. In the drawings, like reference numerals represent like parts throughout the several views FIG. 1 illustrates an oxygenator 10 for oxygenating blood, in accordance with many embodiments. The oxygenator 10 includes a housing 100 within which an oxygenator assembly 200 is disposed. The oxygenator assembly 200 includes a blood inlet 201, a blood outlet 202, an oxygenation chamber 203, and elongated gas permeable conduits 210 that extend across the oxygenation chamber 203. For example, the elongated gas permeable conduits 210 may be a bundle of hollow fibers, whose hollow ends extend across a width W1 (e.g., from left to right) and the bundle extend along a length L1 in the direction of the blood flow. In other words, the hollow ends of the elongated gas permeable conduits 210 do not extend along the length L1 of the oxygenator assembly 200. In many embodiments, the oxygenator 10 may be cylindrical in shape. Accordingly, the housing 100 may be substantially cylindrical in shape, and the elongated gas permeable conduits 210 may be configured to have cylindrical, cuboid, prismatic (e.g., hexagonal, octagonal, or higher order), or other shapes.

The oxygenator assembly 200 is configured so that a blood flow received via the blood inlet 201 is contacted with exterior surfaces of the elongated gas permeable conduits 210 and exits the oxygenator assembly 200 through the blood outlet 202. In the illustrated embodiments, the blood flows along z-axis or along the length L1 of the elongated gas permeable conduits 210. Each of the elongated gas permeable conduits 210 include a gas permeable outer wall configured to accommodate transfer of oxygen from within the elongated gas permeable conduits 210 to the blood flow and transfer carbon dioxide from the blood flow into the elongated gas permeable conduits 210. Among the elongated gas permeable conduits 210, a first set of the elongated gas permeable conduits is oriented parallel to a first direction, and a second set of the elongated gas permeable conduits is oriented parallel to a second direction that is transverse or opposite to the first direction. As an example, the opposite direction indicates 180° or not angled, with respect to the first direction. In some examples, the second direction or the transverse direction indicates a direction at an angle (e.g., 5°, 10°, 15°, etc.) other than 90° with respect to the first orientation.

The housing 100 surrounds the oxygenator assembly 200 and includes a gas inlet 101 and a gas outlet 102. The housing 100 is configured to distribute a gas flow received through the gas inlet 101 to the elongated gas permeable conduits 210 so as to flow through a first set of the elongated gas permeable conduits 210 in a first direction D1 (e.g., from left to right) and flow through a second set of the elongated gas permeable conduits 210 in a second direction D2 (e.g., from right to left) that is opposite to the first direction D1. For example, the first direction D1 is along 0° and the second direction D2 is along 180° with respect to the first direction D1. However, the present disclosure is not limited to 180° opposite direction. For example, the first set of conduits can allow the gas flow in the first direction D1 and the second set of conduits can allow the gas flow in a transverse direction D2 having an angle within a range from 175° to 185° with respect to the first direction D1. In an illustrated embodiment, the blood flow is perpendicular to the first direction D1 and the second direction D2. In many embodiments, the elongated gas permeable conduits 210 is a bundle of hollow fibers thorough which gas can be passed. In many embodiments, the gas flow includes oxygen or a mixture of gases including oxygen. The gas flow in opposite directions D1 and D2 ensures that the blood is uniformly oxygenated while the blood flows along the length L1. For example, the blood contacting at a left portion and a right portion of the conduits 210 receives oxygen rich gas. Thus, a priming volume of the blood can be substantially reduced and the size of the oxygenator assembly 200 can be small compared to existing oxygenators.

In many embodiments, the housing 100 may include an inlet plenum 111 for temporarily storing gas and delivering the gas to the elongated gas permeable conduits 210 and an outlet plenum 112 for temporarily receiving gas from the conduits 210. In many embodiments, the inlet plenum 111 is configured to receive the gas flow from the gas inlet 101, distribute the first portion of the gas flow to the first inlet chamber (e.g., 601 in FIG. 6), and distribute the second portion of the gas flow to the second inlet chamber (e.g., 603 in FIG. 6). In many embodiments, the outlet plenum 112 is configured to collect the first outlet gas flow from the first outlet chamber (e.g., 602 in FIG. 6), collect the second outlet gas flow from the second outlet chamber (e.g., 604 in FIG. 6), and deliver the first outlet gas flow and the second outlet gas flow to the gas outlet 102. For example, the inlet plenum 111 is configured to receive the gas flow from the gas inlet 101 of the housing 100 and distribute the gas flow to a plurality of chambers (e.g., shown in FIGS. 3-7), each chamber delivering the gas flow to respective first set and/or the second set of the elongated gas permeable conduits 210. The outlet plenum 112 is configured to collect the gas flow from the plurality of chambers and deliver the gas flow to a gas outlet 102 of the housing 100.

In many embodiments, the oxygenation chamber and/or a perimeter of the elongated gas permeable conduits 210 can be configured in circular, square (e.g., see FIG. 2), rectangular, hexagonal (e.g., see FIGS. 3-5) or higher order polygon shape with even numbered sides. In many embodiments, the perimeter of the elongated gas permeable conduits 210 refers to a cross-section shape of the entire bundle of the elongated gas permeable conduits 210 in a plane perpendicular to the flow of blood. The oxygenator assembly 200 herein can employ different configurations of elongated gas permeable conduits 210, further discussed with respect to FIGS. 2-5.

Figure 2A:
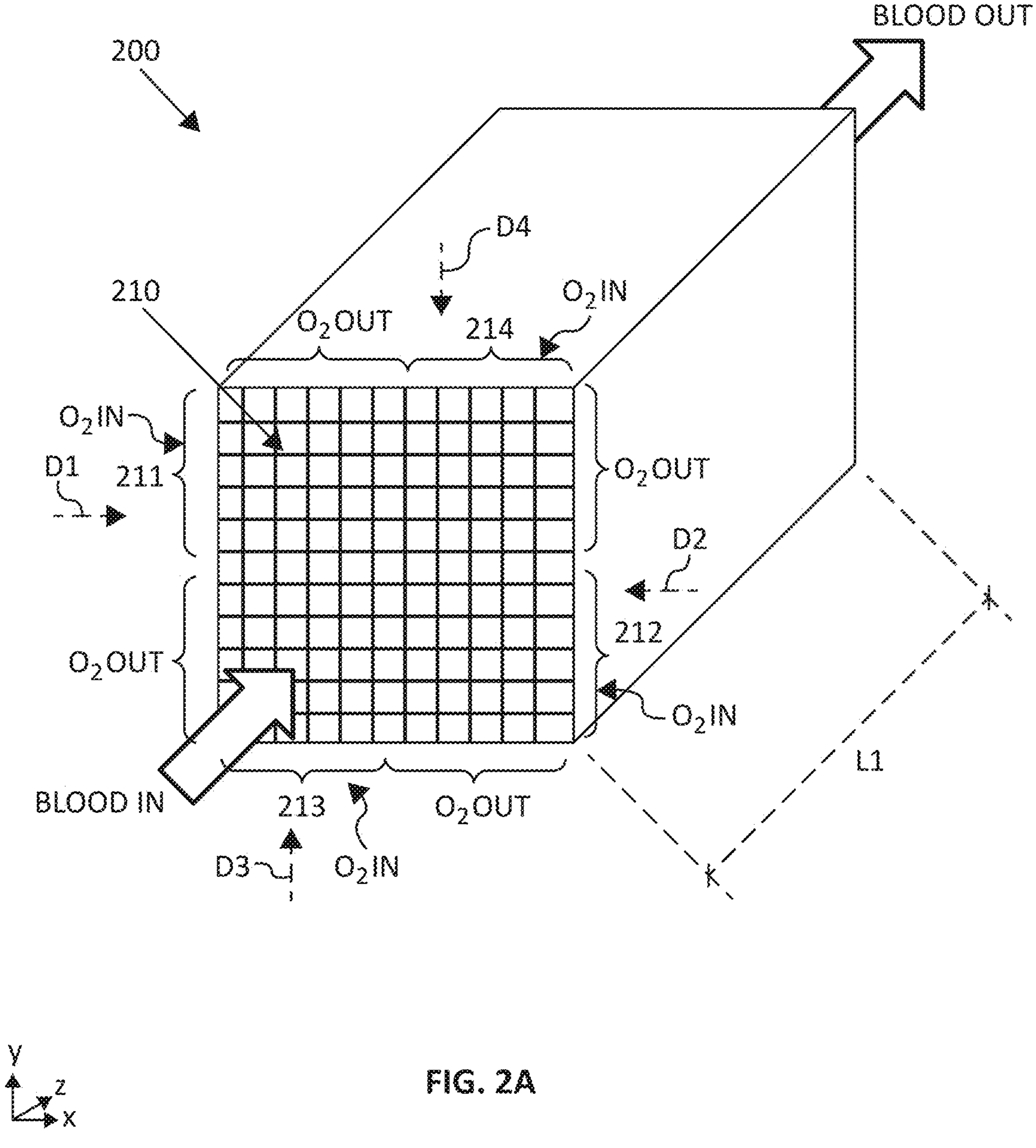
FIG. 2A is a first oxygenator assembly of the oxygenator of FIG. 1.

FIG. 2A is a first oxygenator assembly that can be employed as the oxygenator assembly 200 of the oxygenator of FIG. 1. The elongated gas permeable conduits 210 are configured in a cuboid shape (e.g., the perimeter having rectangular shape) with four sides and extending along a length L1. The conduits 210 can be configured to extend between different sides in such a way that the blood flow is uniformly oxygenated. For example, a first conduit set 211 of the elongated gas permeable conduits 210 extend between a left side and a right side to allow a first portion of the gas flow in a first direction D1. A second conduit set 212 of the elongated gas permeable conduits 210 extend between a left side and a right side to allow a second portion of the gas flow in a second direction D2 that is opposite to the first direction D1. Additionally or alternatively, the elongated gas permeable conduits include a third conduit set 213 and a fourth conduit set 214. The third conduit set 213 extends between a top side and a bottom side to allow a third portion of the gas flow in a third direction D3. The fourth conduit set 214 extends between a top side and a bottom side to allow a fourth portion of the gas flow in a fourth direction D4 that is opposite to the third direction D3. This arrangement is good for local mixing of the blood. Thus, the blood flowing along the length L1 of the elongated conduits 210 is uniformly oxygenated e.g., at least at the sides and at the center of the cross-section as each side includes a gas inlet. For example, the conduits contain the most oxygen near the gas inlet (02 inlet), but is progressively depleted as the gas flows through the conduit toward the gas outlet (02 outlet).

Figure 2B:
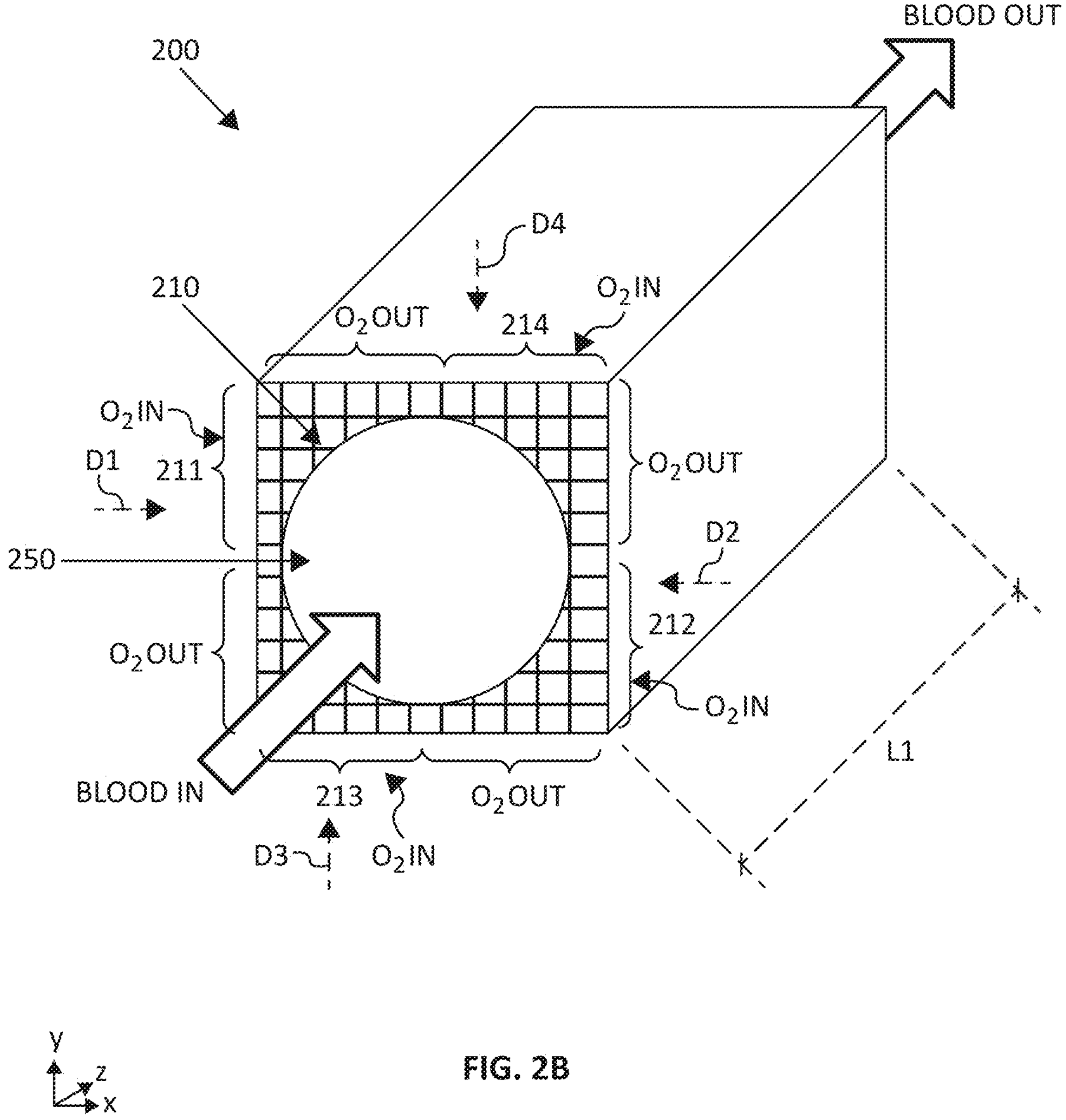
FIG. 2B illustrates the first oxygenator assembly of FIG. 2A having a circular or tubular blood flow path.

FIG. 2B illustrates an oxygenator assembly having a circular or a tubular blood flow path along the length of the oxygenator assembly 200. For example, a circular blood flow cross-section 250 may be created by applying potting at the corner and sides of the cuboid shape to create the circular blood flow cross-section 250 through which blood can flow. In the illustrated embodiment, oxygen is more uniformly distributed into the blood flow as oxygen is being supplied in opposite directions (e.g., D1 and D2, and D3 and D4) at several locations along the circumference of the circular cross-section 250 compared to oxygen being supplied only in a single direction.

The elongated gas permeable conduits 210 is not limited to a number of conduit sets. It can be understood that the elongated gas permeable conduits 210 can include a first conduit set, a second conduit set, a third, conduit set, a fourth conduit set, or more number of conduit sets, wherein a pair of conduit sets are configured to direct gas in opposite directions (e.g., D1 and D2, D3 and D4, etc.). In many embodiments, each of the conduit set may be oriented at same or different angles with respect to each other. In some embodiments, the elongated gas permeable conduits 210 include a plurality of layers stacked against each other in the blood flow direction. Each layer includes a subset of conduits of the elongated gas permeable conduits 210 that are offset from each other. Example configuration of different set of conduits and/or layers is further illustrated and discussed with respect to FIGS. 3-5.

Figure 3:
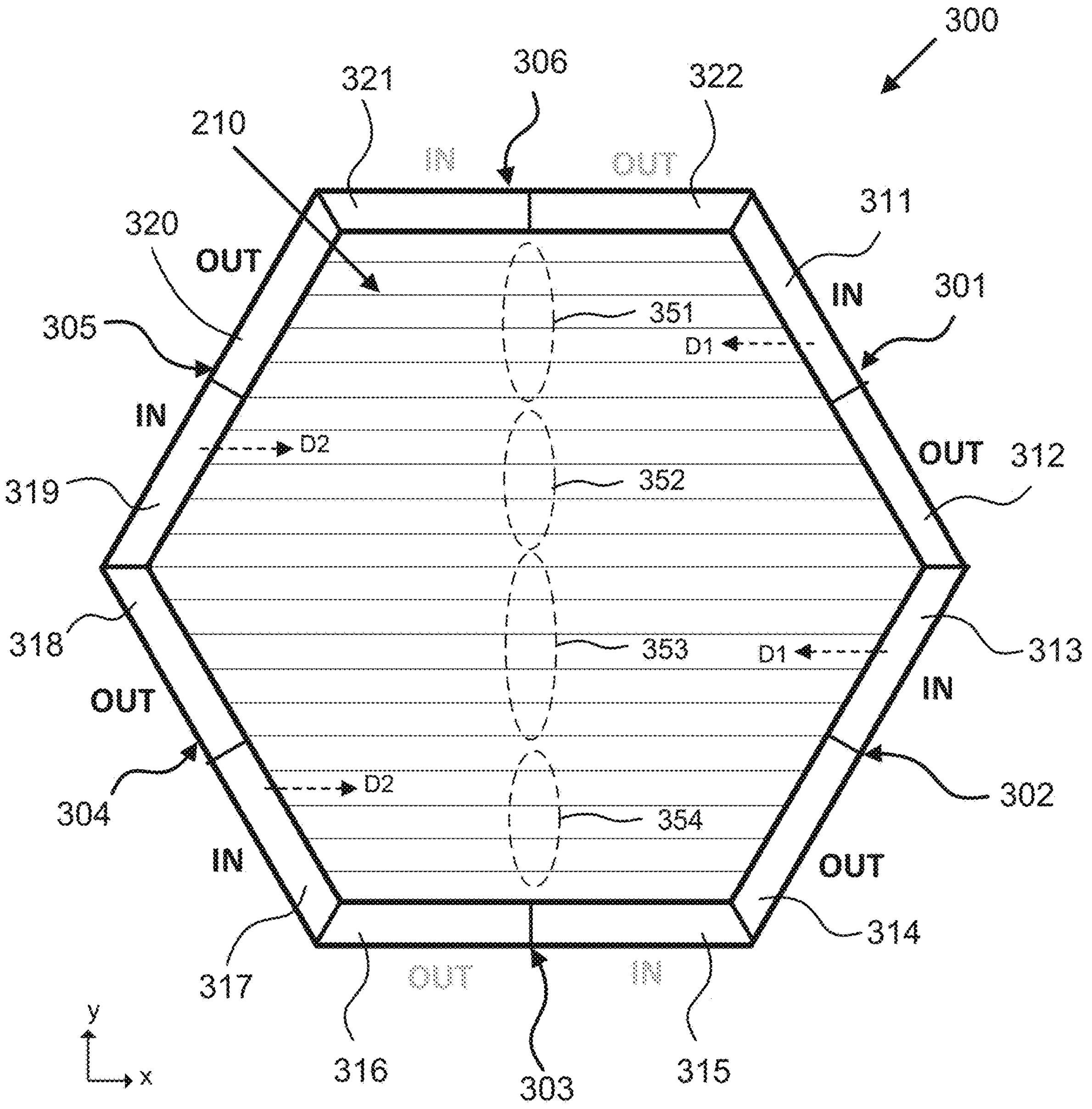
FIG. 3 illustrates gas permeable conduits of a first layer of a second oxygenator assembly of the oxygenator of FIG. 1.
Figure 4:
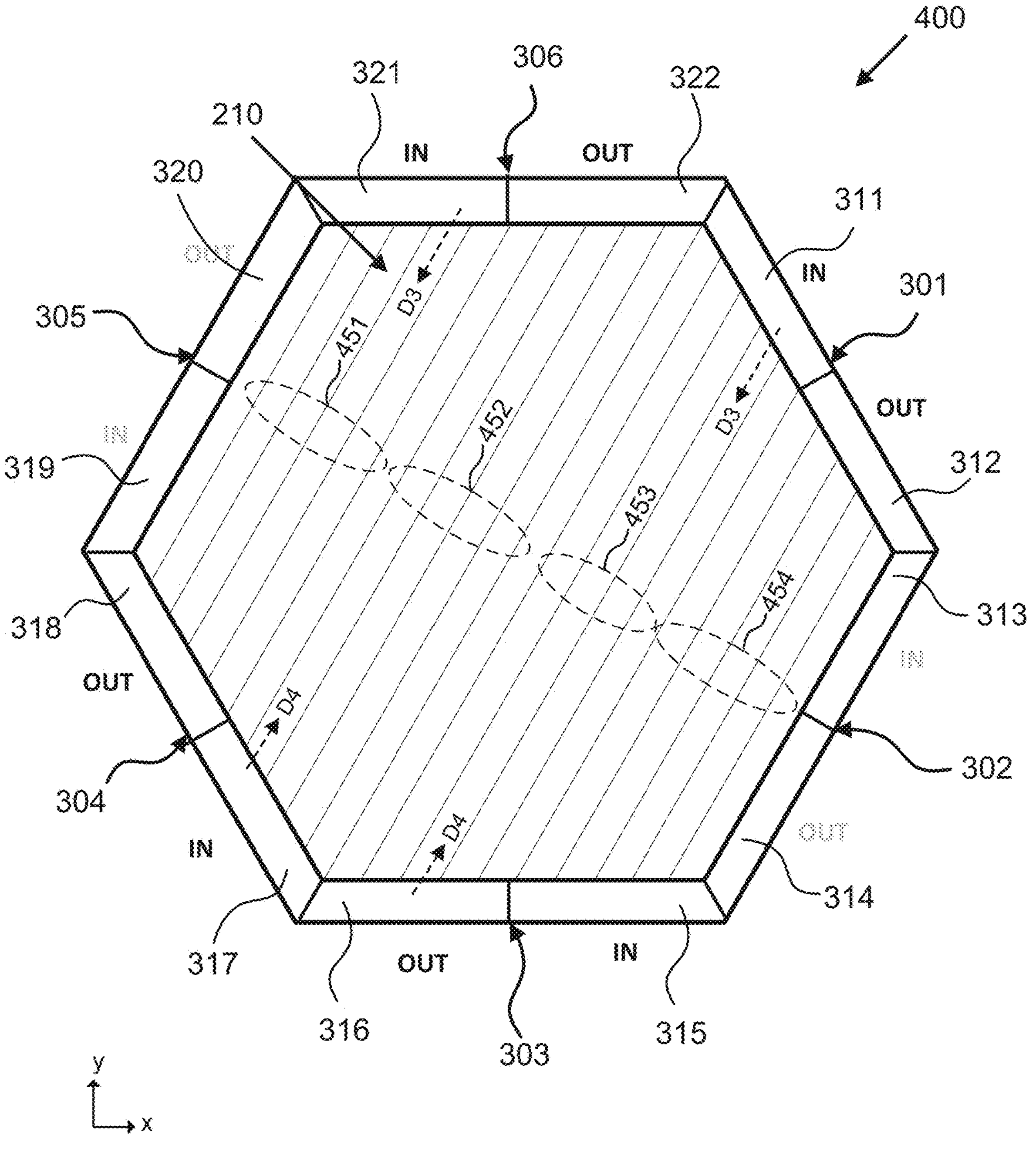
FIG. 4 illustrates gas permeable conduits of a second layer of the second oxygenator assembly of the oxygenator of FIG. 1.
Figure 5:
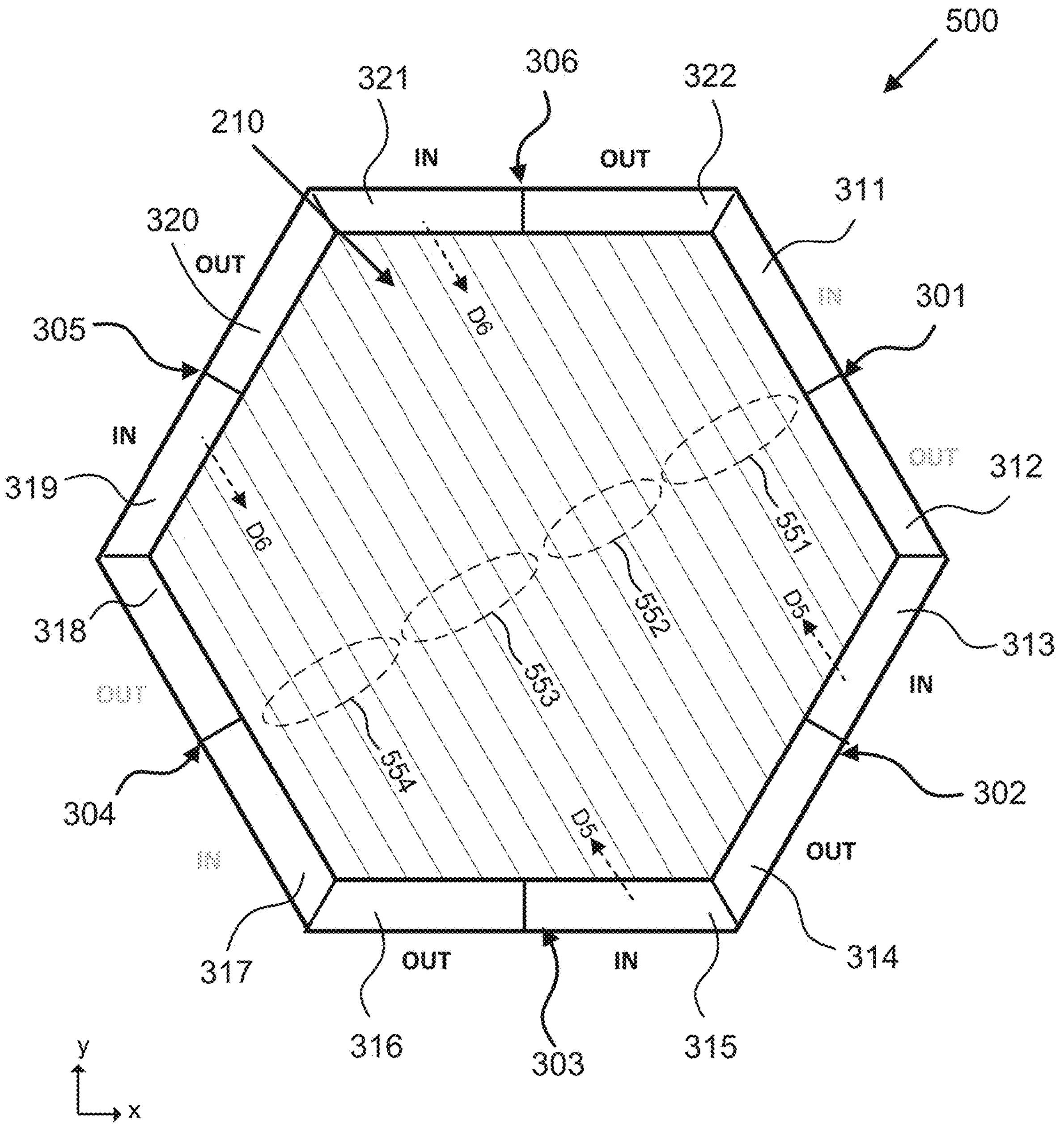
FIG. 5 illustrates gas permeable conduits of a third layer of the second oxygenator assembly of the oxygenator of FIG. 1.

FIG. 3 is a first layer 300 that can be employed in the oxygenator assembly 200. FIG. 4 is a second layer 400 that can be employed in the oxygenator assembly 200. FIG. 5 is a third layer 500 that can be employed in the oxygenator assembly 200. Each of the layers 300, 400, 500 include conduit sets that are oriented at different angles with respect to another layer. The elongated gas permeable conduits 210 can include one or more of the first layers 300, one or more of the second layer 400, and one or more of the third layer 500 stacked against each other in the blood flow direction. For example, the first layer 300 may be disposed as the first, fourth, seventh, etc. layer. Similarly, the second layer 400 may be disposed as the second, fifth, eighth, etc. layer, and the third layer 500 may be disposed as the third, sixth, ninth, etc. layer. Accordingly, at least one layer includes a subset of conduits has an angular orientation different from another subset of conduits of at least another layer. For example, conduits in the second layer 400 are oriented at 60° with respect to conduits in the first layer 300. Conduits in the third layer 500 are oriented at 120° with respect to the first layer 300. This arrangement is good for local micro-scale mixing of oxygen with the blood at different locations along the blood flow. The present disclosure is not limited to angular orientations illustrated, and other angles are possible. For example, the fibers can be at oriented at angles in a range between 5° to 10° with respect to hexagon axes and yet connected to respective inlet and outlet chambers. Also, other shapes of the oxygenator assembly are possible. For example, the shape can be an irregular hexagon having equal or unequal lengths, or other polygonal shapes.

In the illustrated embodiments of FIGS. 3-5, the elongated gas permeable conduits 210 has a hexagonal cross-section (e.g., in a plane perpendicular to the blood flow) and can be configured to form a hexagonal prism that can be disposed in the oxygenator assembly 200 (in FIG. 1). As shown, the hexagonal form has a first side 301, a second side 302, a third side 303, a fourth side 304, a fifth side 305, and a sixth side 306. Each of the sides 301-306 is configured to include a gas input (IN) and a gas output (OUT). The input IN and output OUT of each side can be coupled to chambers to receive or deliver gas therein. For example, at the first side 301, a first gas input at can be coupled to a first chamber 311 and a first gas output can be coupled to a second chamber 312. At the second side 302, a second gas input can be coupled to a third chamber 313 and a second gas output can be coupled to a fourth chamber 314. At the third side 303, a third gas input can be coupled to a fifth chamber 315 and a third gas output can be coupled to a sixth chamber 316. At the fourth side 304, a fourth gas input can be coupled to a seventh chamber 317 and a fourth gas output can be coupled to an eighth chamber 318. At the fifth side 305, a fifth gas input can be coupled to a ninth chamber 319 and a fifth gas output can be coupled to a tenth chamber 320. At the sixth side 306, a sixth gas input can be coupled to an eleventh chamber 321 and a sixth gas output can be coupled to a twelfth chamber 322.

In FIG. 3, the first layer 300 of the elongated gas permeable conduits 210 includes first conduit sets 351 and 353 oriented to pass gas therethrough in the first direction (e.g., D1) and second conduit sets 352 and 354 oriented to pass gas therethrough in the second direction (e.g., D2) opposite to the first direction. The first conduit sets 351 and 353 are separated by the second conduit set 352 and 354, respectively. In the illustrated embodiment, based on the direction of gas flow, each of the first conduit sets 351, 353 are oriented at 0° and the second conduit sets 352, 354 are oriented at 180°. The first conduit sets 351 and 353 receive gas from the first gas chamber 311 and the third gas chamber 313, respectively, and output the gas to the tenth gas chamber 320 and the eighth gas chamber 318, respectively. Similarly, the second conduit sets 352 and 354 receive gas from the ninth gas chamber 319 and the seventh gas chamber 317, respectively, and output the gas to the second gas chamber 312 and the fourth gas chamber 314, respectively.

In FIG. 4, the second layer 400 of the elongated gas permeable conduits 210 includes third conduit sets 451 and 453 oriented to pass gas therethrough in a third direction D3 and fourth conduit sets 452 and 454 oriented to pass gas therethrough in a fourth direction D4 opposite to the third direction D3. The third conduit sets 451 and 453 are separated by the fourth conduit sets 452, 454, respectively. In the illustrated embodiment, each of the third conduit sets 451, 453 are oriented to deliver gas at 60° (e.g., with respect to the first direction D1) and the fourth conduit sets 452, 454 are oriented to deliver gas at −60°. As discussed earlier, the present disclosure is not limited to illustrated angles and other angles are possible. The third conduit sets 451, 453 receive gas from the eleventh gas chamber 321 and the first gas chamber 311, respectively, and output the gas to the eighth gas chamber 318 and the sixth gas chamber 316, respectively. Similarly, the fourth conduit sets 452, 454 receive gas from the seventh gas chamber 317 and the fifth gas chamber 315, respectively, and output the gas to the twelfth gas chamber 322 and the second gas chamber 312, respectively.

In FIG. 5, the third layer 500 of the elongated gas permeable conduits 210 includes fifth conduit sets 551 and 553 oriented to pass gas therethrough in the fifth direction D5 and sixth conduit sets 552 and 554 oriented to pass gas therethrough in the sixth direction D6 opposite to the first direction. The fifth conduit sets 551 and 553 are separated by the sixth conduit sets 552 and 554, respectively. In the illustrated embodiment, each of the fifth conduit sets 551, 553 are oriented to direct the gas flow at 120° (e.g., with respect to the first direction D1) and the sixth conduit sets 552, 554 are oriented to direct the gas flow at −120°. As discussed earlier, the present disclosure is not limited to illustrated angles and other angles are possible. The fifth conduit sets 551, 553 receive gas from the third gas chamber 313 and fifth gas chamber 315, respectively, and output the gas to the twelfth gas chamber 322 and the tenth gas chamber 320, respectively. Similarly, the sixth conduit sets 552, 554 receive gas from the eleventh gas chamber 321 and the ninth gas chamber 319, respectively, and output the gas to the fourth gas chamber 314 and the sixth gas chamber 316, respectively.

According to the illustrated configuration in FIGS. 3-5, one gas chamber can deliver gas to conduit sets oriented at different angles in respective layers 300-500. Similarly, one gas chamber can receive gas from conduit sets oriented at different angles in the respective layers 300-500. The housing 100 can be configured (e.g., via the inlet plenum) to direct the gas from the gas inlet 101 to the respective chambers IN (in FIGS. 3-5) to cause effective distribution of oxygen to the blood flow. Additional or alternatively, the housing 100 can be configured (e.g., via the outlet plenum) to direct the gas from the respective chambers OUT (in FIGS. 3-5) to the gas outlet 102.

Figure 6:
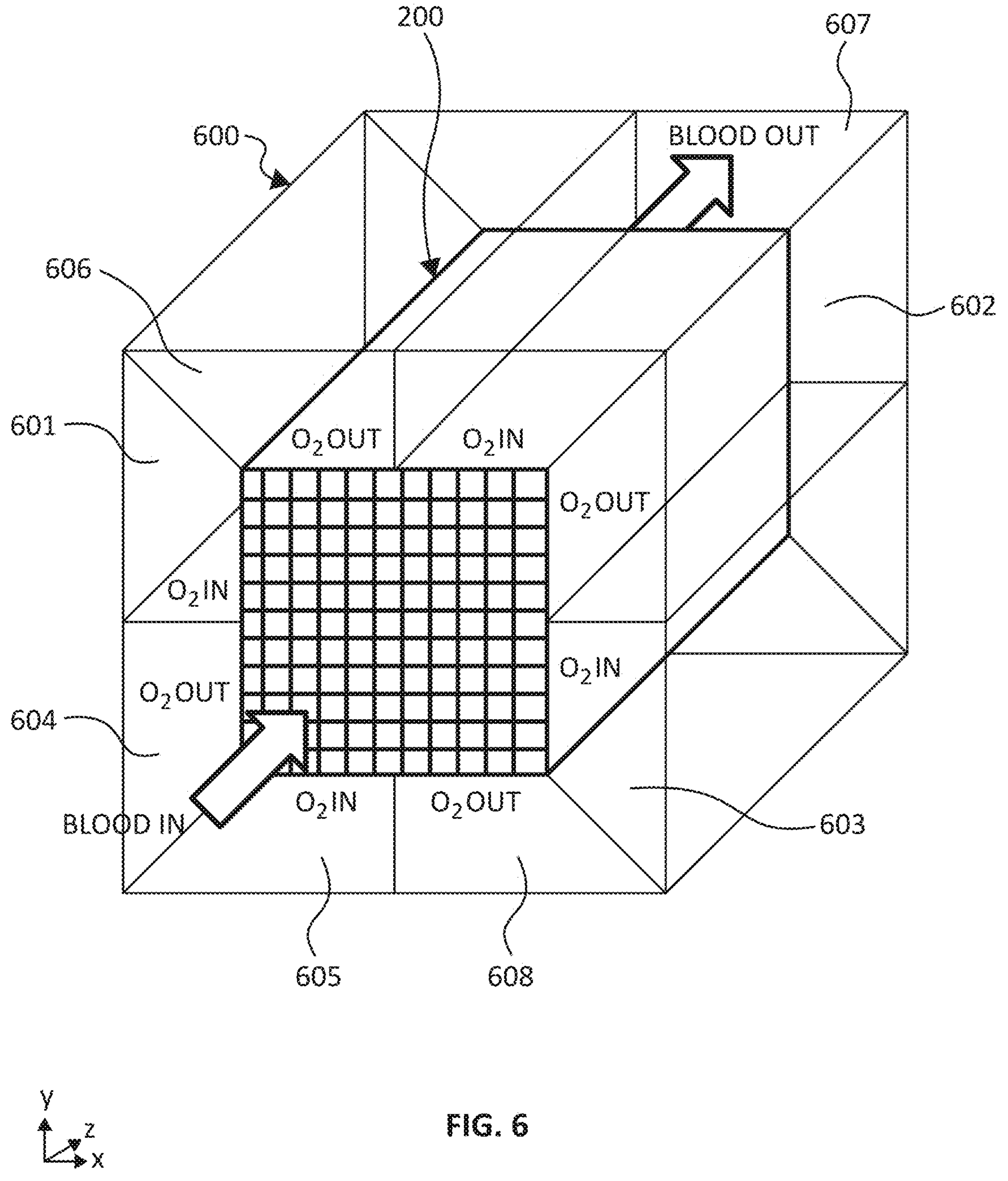
FIG. 6 illustrates a first housing for the first oxygenator assembly of FIG. 2.
Figure 7:
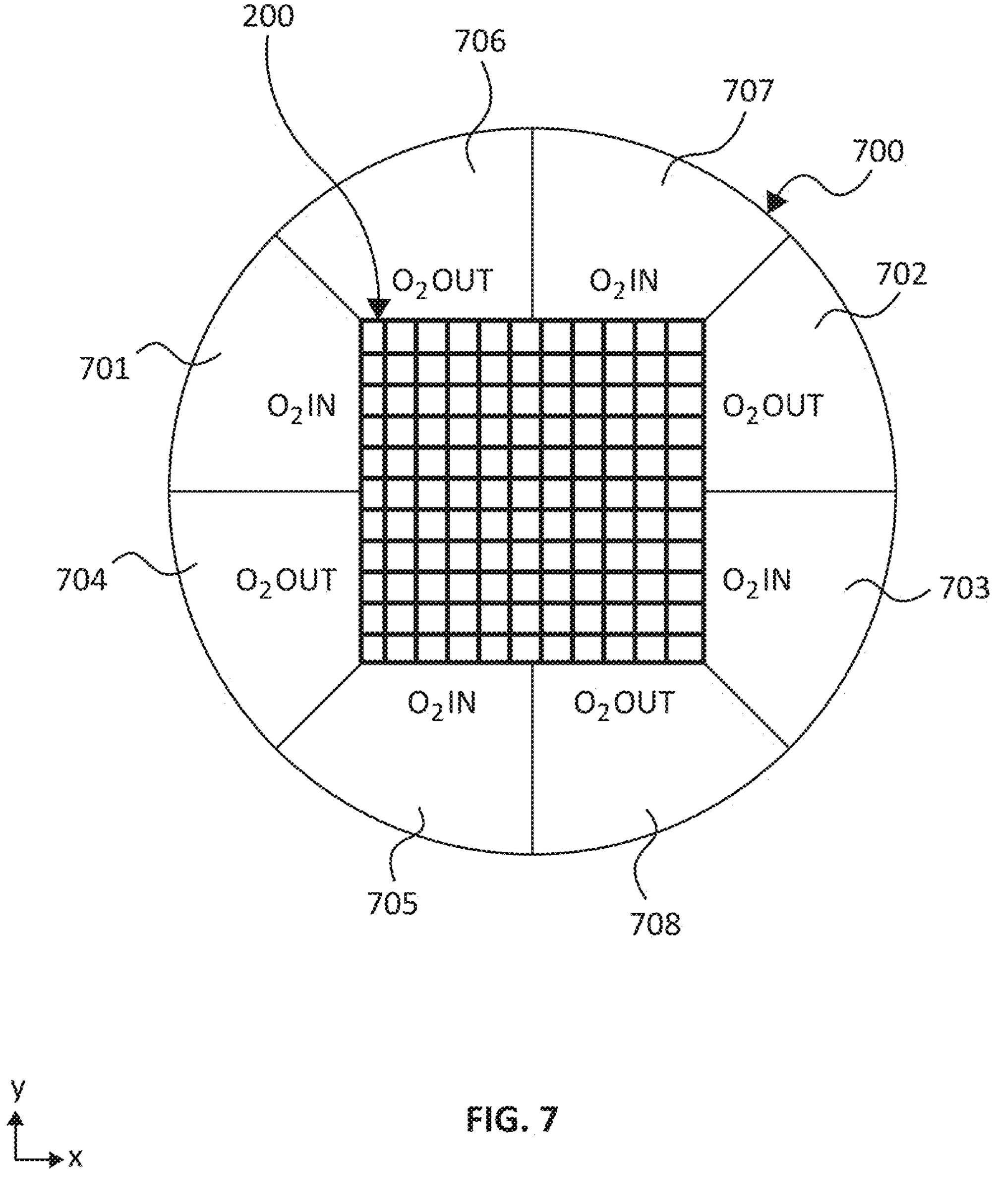
FIG. 7 illustrates a second housing for the first oxygenator assembly of FIG. 2.

FIG. 6 illustrates a first example housing 600 and FIG. 7 illustrates a second example housing 700 that can be used for the first oxygenator assembly 200 of FIG. 2. Each of the housings 600 and 700 include a plurality of chambers isolated from each other and configured to distribute portions of the gas flow to respective sets of conduits. The shapes of the chambers however can be different. For example, the chambers of the housing 100 have substantially cuboid shape, and the chambers of the housing 700 have a substantially cylindrical shape. Additionally, the blood flow path can be configured to have a cuboid, a circular or other shapes without limiting the scope of the present disclosure. For example, shape of the blood flow path across the fibers can be formed by applying a potting compound e.g., at the corners of a cuboid to form a circular shape (e.g., as shown in FIG. 2B).

In FIG. 6, the housing 600 includes a first inlet chamber 601 delivering a first portion of the gas flow to the first conduit set 211, a first outlet chamber 602 receiving the first outlet gas flow exiting from the first conduit set 211, a second inlet chamber 603 delivering a second portion of the gas flow to the second conduit set 212, and a second outlet chamber 604 receiving the second outlet gas flow exiting from the second conduit set 212. Similarly, inlet chambers 605, 607 are coupled to the conduit sets 213 and 214, respectively, to deliver gas. Outlet chambers 606, 608 to receive gas exiting from the conduit sets 213, 214, respectively. Similar to the housing 600 discussed above, the housing 700 includes a plurality of chambers. These chambers may be arcuate shaped chambers, as illustrated. For example, inlet chambers 701, 703, 705, 707 are coupled to the conduit sets 213 and 214, respectively, to deliver gas. Outlet chambers 702, 704, 706, 708 to receive gas exiting from the conduit sets 213, 214, respectively.

The oxygenator assembly 200 herein has several advantages. The bidirectional gas flow across the blood improves the oxygen distribution across the blood compared to other gas flow arrangements (e.g., FIGS. 8 and 9 discussed later). For example, conduits 211 and 212, 213 and 214, 351-354, 451-454, and 551-554 facilitate the bidirectional flow to provide uniformly infuse the blood with oxygen. A uniform distribution of the oxygen enables a smaller priming volume of the blood, less shear stress on the blood, and lower blood pressure drop across the oxygenator.

Figure 8:
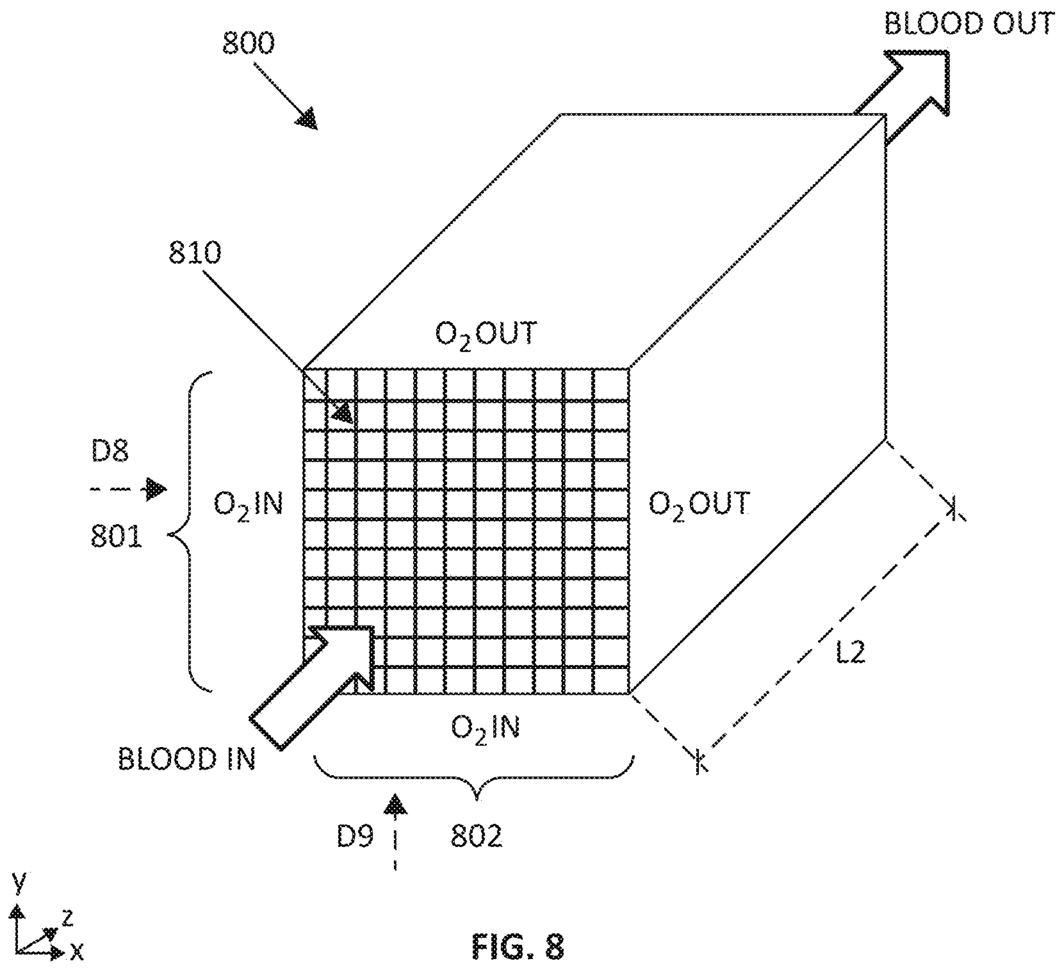
FIG. 8 illustrates another oxygenator assembly, according to some embodiments.

FIG. 8 illustrates another oxygenator assembly 800, where gas flows in one direction but there is no gas flow in an opposite direction. The oxygenator assembly 800 includes another elongated gas permeable conduits 810 arranged to include a tenth conduit set 801 to pass gas in a direction D8 (e.g., left to right) and an eleventh conduit set 802 configured to direct gas in a perpendicular direction D9 to the direction D8. This arrangement of the conduits 810 exposes different portions of the blood flow to a different amount of available oxygen compared to the gas distribution caused by arrangements shown in FIGS. 1-7.

Figure 9:
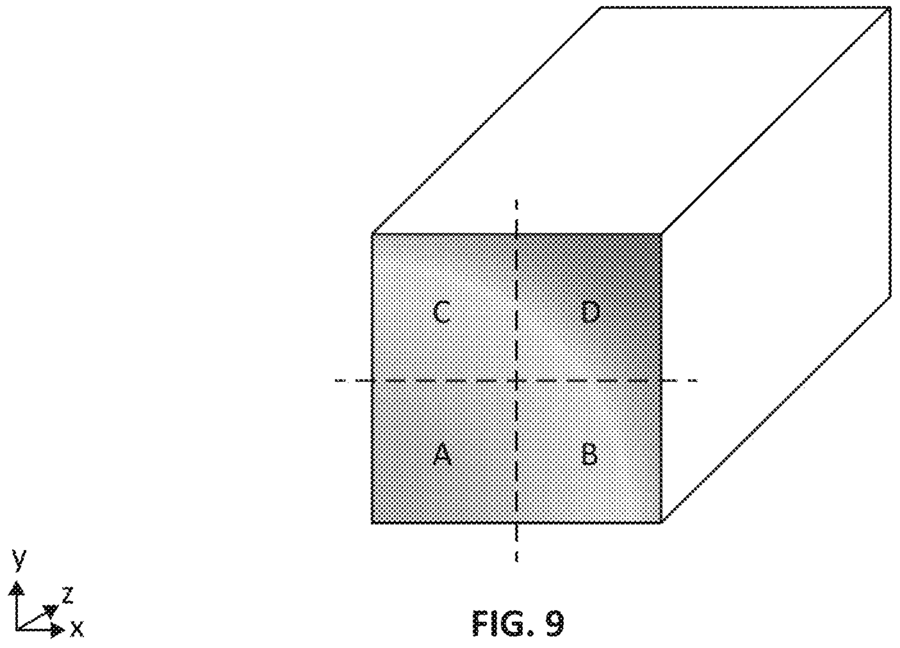
FIG. 9 illustrates oxygen distribution of the blood flowing through the oxygenator assembly of FIG. 8.

FIG. 9 illustrates oxygen distribution of the blood flowing through the another oxygenator assembly 800. The arrangement of conduits 810 (e.g., the tenth conduit set 801, and the eleventh conduit set 802) contain the most oxygen near the gas inlet, but are depleted as the gas flows down the length of the tenth conduit set 801. For example, oxygen distribution a cross-section of the elongated conduits 810 perpendicular to the blood flow is explained in reference to quadrants A, B, C, and D. Quadrant A corresponds to portions of the conduit sets 801 and 802 where both directions D8 and D9 are near gas inlet. Two quadrants B and C correspond to one portion of the conduit set is near a gas inlet, but other portion of the conduit set is near the gas outlet, far from the inlet. Quadrant D correspond to portions of the conduit sets 801, 802, where all conduits are gas outlets far from the inlets. As such, the blood traveling down the oxygenator in quadrant A is quickly oxygenated from the available oxygen in nearby conduits. In quadrant D, the blood is initially only slowly oxygenated. Sufficiently far down a length L2 of the oxygenator assembly 800, when quadrant A blood is saturated, oxygen reaches quadrant D in higher concentrations, completing pick up of oxygen in D quadrant. The disadvantage of such arrangement is that the oxygenator length L2 needs to be longer than the length L1 of the oxygenator assembly 200, where the oxygen distribution is more uniform across the blood flow cross-section. As such, the oxygenator assembly 800 leads to a larger priming volume, more shear on the blood, and a larger pressure drop, all of which are undesired.

Figure 10:
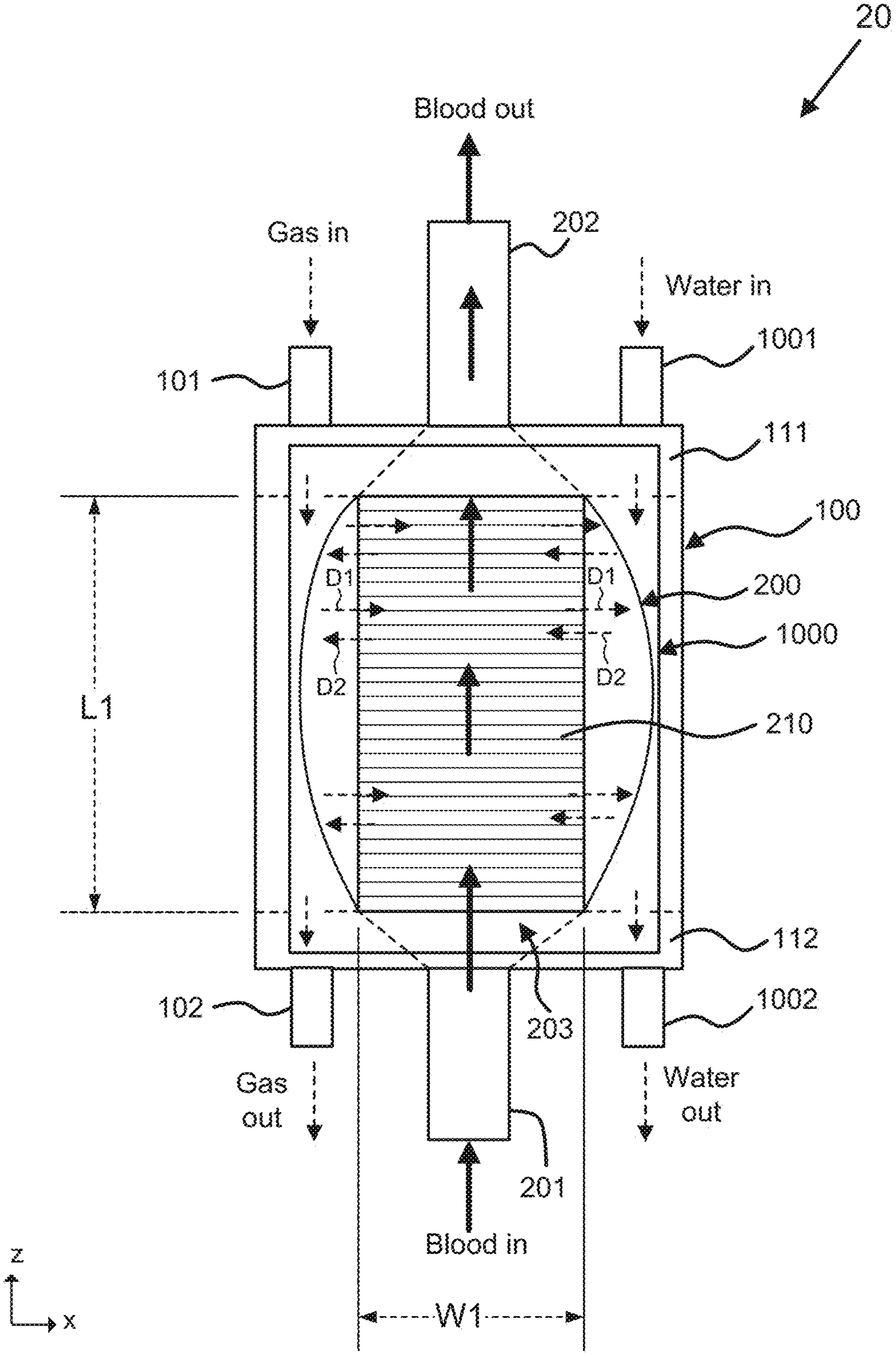
FIG. 10 is another oxygenator including a heat exchanger coupled to the oxygenator assembly of FIG. 1.

FIG. 10 is another oxygenator 20 including the oxygenator assembly 200 of FIG. 1 and a heat exchanger 1000. The oxygenator 20 has substantially similar configuration as the oxygenator assembly 200 including the elongate gas permeable conduits 210 and additionally surrounded by the heat exchanger 1000. The heat exchanger 1000 is disposed within the housing 100 and configured to regulate a temperature of the flow of blood by passing temperature regulation fluid around the oxygenator assembly 200. For example, the temperature regulation fluid may be gaseous or liquid coolant (e.g., water). In one embodiment, the heat exchanger 1000 is configured in a similar manner to as gas distribution (e.g., the bidirectional gas flow) through the housing 100.

The heat exchanger 1000 includes a temperature regulation fluid inlet 1001, a temperature regulation fluid outlet 1002, and heat exchanger conduits (e.g., pipes). A first set of the heat exchanger conduits is oriented parallel to a heat exchanger conduit first direction (e.g., along the direction D1) and a second set of heat exchanger conduits is oriented parallel to a heat exchanger conduit second direction (e.g., along the direction D2) that is transverse or opposite to the heat exchanger conduit first direction. The heat exchanger 1000 is configured so that the blood flow received via the blood inlet 201 is contacted with exterior surfaces of the heat exchanger conduits, a first portion of a flow of temperature regulation fluid received through the temperature regulation fluid inlet 1001 flows through the first set of the heat exchanger conduits in the first direction D1, and a second portion of the flow of temperature regulation fluid flows through the second set of the heat exchanger conduits in the second direction D2. Accordingly, the blood can be cooled uniformly in a similar manner to the uniform gas distribution in the blood.

Figure 11:
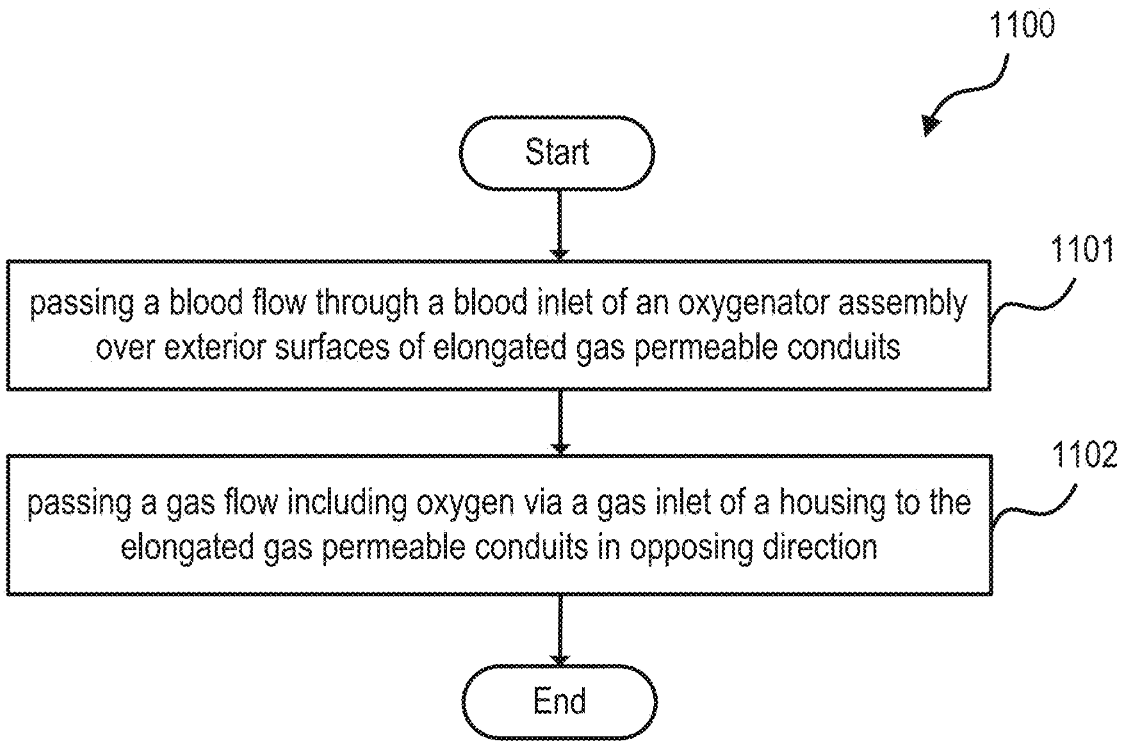
FIG. 11 is a flow chart of a method of oxygenating blood using an oxygenator of FIG. 1, according to many embodiments.

FIG. 11 is a flow chart of a method 1100 of oxygenating blood using the oxygenator, according to various embodiments of the present disclosure. The oxygenator (e.g., 10 in FIG. 1 configured to include the elongated gas permeable conduits 210) facilitates uniform oxygen distribution to the blood as it travel through the oxygenator that provides advantages such as reduced priming volume, shear stress, compact oxygenator design (e.g., small axial length L1), or other advantages. The method includes example steps 1101 and 1102. As discussed herein, the elongated gas permeable conduits are oriented in opposing directions (e.g., angular or opposite direction) so that oxygen is more uniformly distributed in the blood compared to when oxygen is passed in only one direction.

Step 1101 involves passing a blood flow received through a blood inlet of an oxygenator assembly over exterior surfaces of elongated gas permeable conduits that extend across an oxygenation chamber of the oxygenator assembly. For example, as shown in FIG. 1, the blood flow is passed through the blood inlet 201 of the oxygenator assembly 200 including the elongated gas permeable conduits 210. Step 1102 involves distributing a gas flow including oxygen received through a gas inlet of a housing to the elongated gas permeable conduits that a first portion of the gas flow flows through a first set of the elongated gas permeable conduits in a first direction and a second portion of the gas flow flows through a second set of the elongated gas permeable conduits in a second direction that is transverse to or opposite to the first direction to transfer oxygen from the gas flow to the blood flow and to transfer carbon dioxide from the blood flow to the gas flow. For example, the gas flow is received from the gas inlet 101 of the housing 100 and the gas flow is distributed to the elongated gas permeable conduits 210 configured to direct a first portion (e.g., via the first conduit set 211) of the gas flow in the first direction D1 and a second portion (e.g., via the second conduit set 212) of the gas flow in the second direction D2 opposite to the first direction D1.

In many embodiments, passing the blood flow includes passing the blood flow in a direction perpendicular to the first direction (e.g., D1) and the second direction (e.g., D2). In many embodiments, passing the gas flow includes passing the gas flow through a plurality of layers (e.g., 300-500 in FIGS. 2-5) of the elongated gas permeable conduits (e.g., 210). For example, a first layer (e.g., 300) includes the first conduit set and the second conduit set, a second layer (e.g., 400) includes a third conduit set and a fourth conduit set that are oriented at a first angle with respect to the conduits of the first layer (e.g., 300), and a third layer (e.g., 500) includes the fifth conduit and a sixth conduit set that are oriented at a second angle with respect to the first layer (e.g., 300).

The oxygenator assembly herein can be implanted in different medical applications. For example, an oxygenator system or other systems requiring oxygenation of the blood. In some embodiments, an oxygenator system (e.g., 1200 in FIG. 12) includes the oxygenator 10 of FIG. 1 that facilitates the oxygenator system to be compact, requiring smaller priming volume, and advantages associated with integration of the oxygenator 10. In some embodiments, the oxygenator 10 may be integrated with a pump, such as discussed in U.S. Pat. No. 10,258,729. In addition, the oxygenator system may include one or more accessories as follows:

Ultrasonic Flow Probe—This device measures blood flow as it flows through the tubing out from and/or into the oxygenator. Current technology (Transonic Flow Probe—PXL series) enables a box-like sensor to be placed about the tubing and assesses the blood non-invasively. This device (or equivalent) is electronically integrated into the CentriMag Electronic Controller providing feedback for blood flow control.

Temperature Probe—This device measures blood temperature returning to the patient and alerts the user if excessive heat loss occurs. When combined with a blood heat exchanger device, normothermic blood temperature may be maintained should excessive heat loss occur.

Blood Heat Exchanger—This is typically a water-based shell and tube-type heat exchanger that controls the blood temperature as it circulates in or about the heat exchanger core. Although improvements in technology can provide over-temperature protection from over-heating the blood (above 42° C.), water (or other medium) provides another level of safety over direct temperature control. As such, a heat exchanger controller maintains set temperature from a larger mass of water built into the controller device. A blood heat exchanger device may be integrated in the pump-oxygenator or a separate device, positioned before the oxygenator bundle (preferred). Such a device may be positioned before the blood inflow of the pump-oxygenator. Regardless of the design configuration, the water and blood phases must be structurally separated.

Compliance Chamber—This is typically utilized when there are expected changes in the vasculature. Medically induced vasoconstrictors can dramatically affect blood pressure. A compliant chamber placed in series to the patient can absorb the extra volume resulting from constriction of a closed system. More typically, in ECMO utilization, the patient is effectively their own reservoir and a compliance chamber may not be required.

Blood Reservoir—This is a holding chamber for excess blood. This device is critical for open heart surgery or trauma where blood losses, large blood temperature swings and medicines require extra volume storage. The pump-oxygenator may be adapted to contain or affix a blood reservoir, but for ECMO utilization a reservoir is not required.

Blood-Gas Sensors—These are devices utilized to assess real-time blood gases ($O_2$ and $CO_2$). Special connectors are required of Blood-Gas manufacturers and they may be integrated into the device for sensor connection or placed in-line on the tubing set connected to the pump-oxygenator device.

Prime Circuit—This is a sterile tube pack that enables the user to rapidly set up and prime the by-pass circuit, interconnecting the saline priming solution bags/containers to the pump-oxygenator device. This circuit is connected to the inflow connector and outflow connector and permits fluid circulation to de-bubble and prime the extracorporeal circuit. Alternative embodiments may address the designs, applications, materials, coatings, uses, accessories, construction processes, costs, etc.

Figure 12:
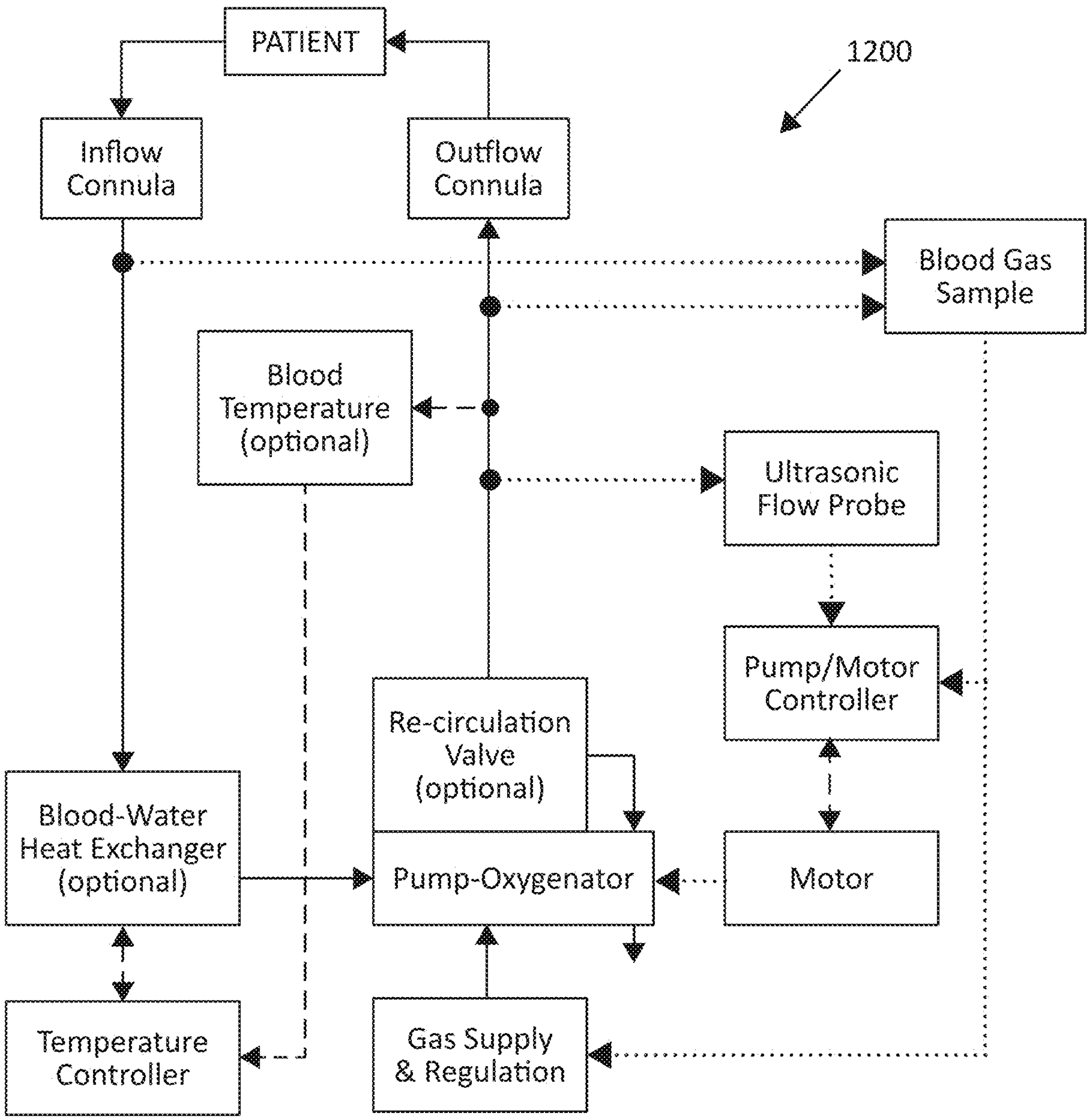
FIG. 12 is a block diagram of an example of a blood oxygenator control system in accordance with many embodiments.

FIG. 12 is an example of a diagram of a blood oxygenator control system for controlling an extracorporeal life support system 1200 including the oxygenator 10 or 20 in accordance with the present disclosure. Any suitable inflow and outflow cannulae and tubing can be used as are known in the art. The extracorporeal life support system 1200 (ECLS) preferably is sized and configured to be positionable beneath or adjacent to a patient treatment table or operating table. A pump driven oxygenator and a motor can be attached to a vertical pole or other support.

The extracorporeal life support system 1200 can comprise a blood flow probe, such as an ultrasonic flow probe, connected to the pump/motor controller. The flow probe measures blood flow as it flows through the tubing out from or into the device. Any suitable ultrasonic flow probe can used as in the art. For example, a box-like sensor, such as the Transonic Flow Probe (such as those commercially available from Harvard Apparatus, Holliston, Mass.), can be placed about the tubing to assess blood flow non-invasively. The flow probe can be electronically integrated into the pump/motor controller to provide feedback for blood flow control.

The extracorporeal life support system 1200 can comprise a compliance chamber (not shown in FIG. 12) between a patient, to whom the extracorporeal life support system 1200 is attached, and the extracorporeal life support system 1200. A compliance chamber is typically used when there is an expected change in the vasculature, such as when a vasoconstrictor is used. A compliance chamber placed in series with the patient can absorb the extra volume resulting from constriction of the vasculature.

If not integrated into the blood pump-oxygenator, a blood gas sensor can be placed in-line on the tubing and a gas supply regulator can be operably connected to the pump/motor controller. If not integrated into the blood pump-oxygenator, a blood heat exchanger can be positioned before the blood flow inlet. A blood temperature probe and a temperature controller then can be operably connected to the blood heat exchanger.

An extracorporeal life support system 1200 may include an integrated centrifugal blood pump-oxygenator and a blood gas sensor in operable communication with the blood inlet and another blood gas sensor in operable communication with the blood outlet, a pump/motor controller, inflow and outflow cannulae and tubing, a motor, and a gas supply regulator, which is operably connected to the pump/motor controller, is also provided.

The blood oxygenator is preferably scalable. The extracorporeal life support system 1200 can be portable and wearable and can be employed in all patients with or without accompanying elevated pulmonary vascular resistance. Such a device would enable a bedridden patient to be ambulatory. If implanted, the housing is desirably made from a biologically compatible material, such as titanium.

It is to be understood that terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures.

What is claimed is:

1. An oxygenator for oxygenating blood, the oxygenator comprising:

an oxygenator assembly comprising a blood inlet, an oxygenation chamber, a blood outlet, and elongated gas permeable conduits that extend across the oxygenation chamber, wherein the oxygenator assembly has a first side, a second side opposite the first side, a length extending between the blood inlet and the blood outlet, and a width extending between the first side and the second side, wherein the elongated gas permeable conduits include a first set of elongated gas permeable conduits having a first inlet at the first side, and a first outlet at the second side, and a second set of elongated gas permeable conduits having a second inlet at the second side and a second outlet at the first side, wherein the oxygenator assembly is configured so that the blood flow received via the blood inlet is contacted with exterior surfaces of the elongated gas permeable conduits and exits the oxygenator assembly through the blood outlet, wherein each of the elongated gas permeable conduits comprises a gas permeable outer wall configured to accommodate transfer of oxygen from within the elongated gas permeable conduit to the blood flow and transfer carbon dioxide from the blood flow into the elongated gas permeable conduits, wherein the first set of the elongated gas permeable conduits is oriented parallel to a first direction; and wherein the second set of the elongated gas permeable conduits is oriented parallel to a second direction that is opposite to the first direction; and a housing comprising a gas inlet and configured to distribute a gas flow received through the gas inlet to the first inlet and the second inlet of the elongated gas permeable conduits so as to flow a first portion of the gas flow through the first set of the elongated gas permeable conduits in the first direction and flow a second portion of the gas flow through the second set of the elongated gas permeable conduits in the second direction.

2. The oxygenator of claim 1, wherein the housing further comprises:

a first inlet chamber configured to deliver the first portion of the gas flow to the first set of the elongated gas permeable conduits; and a second inlet chamber configured to deliver the second portion of the gas flow to the second set of the elongated gas permeable conduits.

3. The oxygenator of claim 2, wherein the housing further comprises:

a first outlet chamber configured to receive a first outlet gas flow exiting from the first set of the elongated gas permeable conduits; and a second outlet chamber configured to receive a second outlet gas flow exiting from the second set of the elongated gas permeable conduits.

4. The oxygenator of claim 3, wherein the housing further comprises:

an inlet plenum configured to receive the gas flow from the gas inlet, distribute the first portion of the gas flow to the first inlet chamber, and distribute the second portion of the gas flow to the second inlet chamber;

a gas outlet; and an outlet plenum configured to collect the first outlet gas flow from the first outlet chamber, collect the second outlet gas flow from the second outlet chamber, and deliver the first outlet gas flow and the second outlet gas flow to the gas outlet.

5. The oxygenator of claim 1, wherein:

a third set of the elongated gas permeable conduits is oriented parallel to a third direction;

the housing is configured to distribute a third portion of the gas flow so as to flow through the third set of the elongated gas permeable conduits in the third direction;

a fourth set of the elongated gas permeable conduits is oriented parallel to a fourth direction that is transverse to the first direction and transverse or opposite to the third direction; and the housing is configured to distribute a fourth portion of the gas flow so as to flow through the fourth set of the elongated gas permeable conduits in the fourth direction.

6. The oxygenator of claim 5, wherein:

the blood flow flows through the oxygenation chamber in a blood flow direction; and the third set and the fourth set of the elongated gas permeable conduits are offset from the first set and the second set of the elongated gas permeable conduits along the blood flow direction or perpendicular to the blood flow direction.

7. The oxygenator of claim 6, wherein the third direction is transverse to the first direction.

8. The oxygenator of claim 1, wherein the oxygenation chamber has a circular, a square, a rectangular, a hexagonal, or an octagonal cross-sectional shape.

9. The oxygenator of claim 1, wherein the elongated gas permeable conduits comprise hollow fibers.

10. The oxygenator of claim 1, further comprising a heat exchanger disposed within the housing and configured to regulate a temperature of the blood flow.

11. The oxygenator of claim 10, further comprising:

a temperature regulation fluid inlet, a temperature regulation fluid outlet, and heat exchanger conduits;

a first set of the heat exchanger conduits is oriented parallel to a heat exchanger conduit first direction;

a second set of the heat exchanger conduits is oriented parallel to a heat exchanger conduit second direction that is transverse or opposite to the heat exchanger conduit first direction;

the heat exchanger is configured so that the blood flow received via the blood inlet is contacted with exterior surfaces of the heat exchanger conduits, a first portion of a flow of temperature regulation fluid received through the temperature regulation fluid inlet flows through the first set of the heat exchanger conduits in the first direction, and a second portion of the flow of temperature regulation fluid flows through the second set of the heat exchanger conduits in the second direction.

12. The oxygenator of claim 1, wherein the blood flow is perpendicular to the first direction and the second direction.

* * * * *